United States Patent [19]

Fleming et al.

[11] 4,073,904
[45] Feb. 14, 1978

[54] BIS-BASIC ETHERS OF 2,6,-AND 2,7-DIHYDROXY-ANTHRAQUINONES

[75] Inventors: Robert W. Fleming; Arthur D. Sill; Francis W. Sweet, all of Cincinnati, Ohio

[73] Assignee: Richardson-Merrell, Inc., Wilton, Conn.

[21] Appl. No.: 652,345

[22] Filed: Jan. 26, 1976

Related U.S. Application Data

[60] Division of Ser. No. 394,584, Sept. 5, 1973, Pat. No. 3,974,186, which is a continuation of Ser. No. 37,312, May 14, 1970, abandoned.

[51] Int. Cl.² .................. C07D 401/10; C07D 403/10; C07D 413/10; A61K 31/445
[52] U.S. Cl. ........................... 424/248.58; 260/272; 260/326.5 C; 424/267; 424/274; 544/79
[58] Field of Search ............... 260/246 B, 293.64, 272, 260/326.5 C; 424/248, 267, 274

[56] References Cited
U.S. PATENT DOCUMENTS

| | | | |
|---|---|---|---|
| 2,881,173 | 4/1959 | Wenner | 260/272 |
| 3,592,819 | 7/1971 | Fleming et al. | 260/246 B |

*Primary Examiner*—Paul M. Coughlan, Jr.
*Attorney, Agent, or Firm*—George W. Rauchfuss, Jr.; Eugene O. Retter

[57] ABSTRACT

Disclosed are novel compounds and pharmaceutical formulations having antiviral activity. The disclosed compounds have the formula

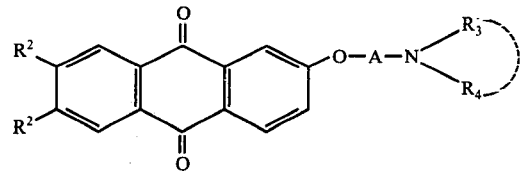

wherein one $R^2$ is a hydrogen atom and the other $R^2$ is the radical

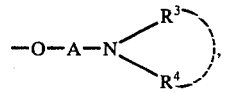

A is a straight chain alkylene group having 2 or 3 carbon atoms and each $R^3$ and $R^4$ is a hydrogen atom, and alkyl radical having 1 to 3 carbon atoms or each set of $R^3$ and $R^4$ taken together with the nitrogen atom to which they are attached is a saturated monocyclic heterocyclic group. Also included are the acid addition salts of these bases. These compounds may be prepared by various methods which are described.

6 Claims, No Drawings

BIS-BASIC ETHERS OF 2,6,-AND 2,7-DIHYDROXY-ANTHRAQUINONES

This is a division of application Ser. No. 394,584, filed Sept. 5, 1973 now U.S. Pat. 3,974,186, which in turn is a continuation of application Ser. No. 37,312, filed May 14, 1970 and now abandoned.

This invention relates to bis-basic ethers of dihydroxyanthraquinones which have useful antiviral properties. More particularly, this invention relates to bis-basic ethers of 2,6- and 2,7-dihydroxyanthraquinones and to antiviral formulations containing the same. This invention also relates to processes whereby said bis-basic ethers of 2,6- and 2,7-dihydroxyanthraquinones and the antiviral formulations containing the same are prepared and also to processes for inhibiting or combatting viral infections.

The novel compounds of this invention are represented by the compounds having the formula

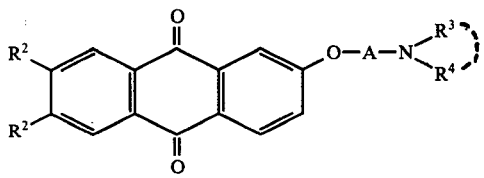

FORMULA 1 wherein one $R^2$ is a hydrogen atom and the other $R^2$ is the radical

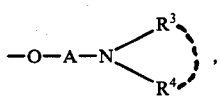

A is a straight chain alkylene group having 2 or 3 carbon atoms and each $R^3$ and $R^4$ is a hydrogen atom, an alkyl radical having 1 to 3 carbon atoms or each set of $R^3$ and $R^4$ taken together with one nitrogen atom to which they are attached is a saturated monocyclic heterocyclic group such as pyrrolidino, piperidino and morpholino. This invention includes both the base form represented by Formula 1 and pharmaceutically acceptable acid salts of the base form as compounds of this invention.

As can be seen from the above Formula 1 and its description, the compounds of this invention can have structures wherein the $R^2$ in the 7 position is a hydrogen atom and the $R^2$ in the 6 position is the radical

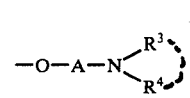

as more fully shown by Formula 2.

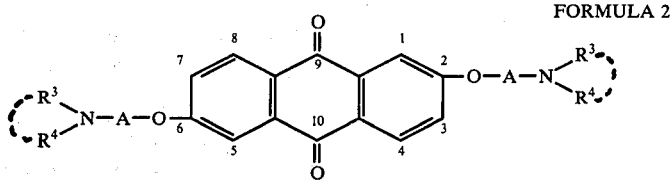

FORMULA 2 or wherein the $R^2$ in the 7 position is the radical

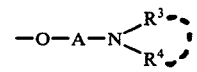

and the $R^2$ in the 6 position is a hydrogen atom as more fully shown by Formula 3.

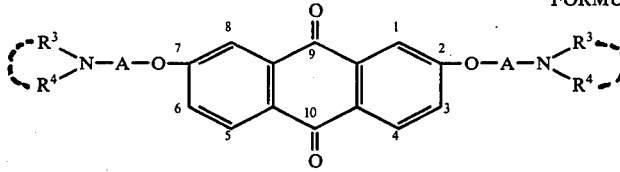

FORMULA 3 wherein $R^3$, $R^4$ and A are as previously defined hereinbefore.

As examples of the radicals which A can represent in compounds of this invention there can be mentioned ethylene and trimethylene. As examples of the radicals which $R^3$ and $R^4$ can represent in compounds of this invention there can be mentioned, hydrogen, methyl, ethyl, propyl and isopropyl and as examples of saturated monocyclic heterocyclic groups which $R^3$ and $R^4$ may represent when taken with the nitrogen atom to which they are attached are pyrrolidino, piperidino and morpholino.

As examples of compounds of this invention which are represented by the formulae and their acid addition salts there may be mentioned for example:

2,6-Bis[2-(diethylamino)ethoxy]anthraquinone dihydrochloride,
2,6-Bis[2-(dimethylamino)ethoxy]anthraquinone dihydrochloride,
2,6-Bis[2-(diisopropylamino)ethoxy]anthraquinone bis hydrogen citrate,
2,6-Bis[2pyrrolidinoethoxy)anthraquinone dihydrochloride,
2,6-Bis(2-piperidinoethoxy)anthraquinone dihydrochloride,
2,6-Bis(2-morpholinoethoxy)anthraquinone dihydrochloride,
2,6-Bis[3-(dimethylamino)propoxy]anthraquinone bis acid maleate,
2,6-Bis[3-(diethylamino)propoxy]anthraquinone dihydrochloride, 2,7-Bis[2-(dimethylamino)ethoxy]anthraquinone dihydrochloride, 2,7-Bis[2-(diethylamino)ethoxy]anthraquinone dihydrochloride, and 2,7-Bis(2-piperidinoethoxy)anthraquinone dihydrochloride.

The pharmaceutically acceptable acid addition salts of the base compounds of this invention are those of any suitable inorganic or organic acids. As examples of suitable acids for preparing the salt form there may be mentioned the following acids in addition to the acids disclosed above, for example, inorganic acids such as hydrochloric, hydrobromic, sulfuric or phosphoric acids and the like as well as suitable organic carboxylic acids, such as, for example, citric, malic, glycolic, lactic, tartaric, malonic, succinic, maleic, fumaric acid and the like.

The compounds of the present invention have utility as the active ingredient in antiviral compositions. The compounds of the present invention can be administered to a host to prevent, inhibit, resist or suppress infections of: picornaviruses, for example, Encephalomyocarditis; myxoviruses, for example Influenza B/Mass.; arboviruses for example, Vesicular Stomatitis; poxviruses, for example, Vaccinia, IHD; and herpesviruses, for example, Herpes simplex. When administered prior to infection, that is, prophylactically, it is preferred that the administration be within about 0 to 48 hours prior to infection of the host animal with the pathogenic virus. When administered therapeutically to inhibit an infection it is preferred that the administration be within about a day or two after infection with the pathogenic virus.

The dosage unit administered will be dependent upon the virus for which treatment or prophylaxis is desired, the type of animal involved, its age, health, weight, extent of infection, kind of concurrent treatment, if any, frequency of treatment and the nature of the effect desired. Illustratively, dosage levels of the administered active ingredients can be: intravenously, 0.1 to about 10 mg/kg; intraperitoneal, 0.1 to about 50 mg/kg; subcutaneous, 0.1 to about 250 mg/kg; orally 0.1 to about 500 mg/kg and preferably about 1 to 250 mg/kg; intranasal instillation, 0.1 to about 10 mg/kg; and aerosol, 0.1 to about 10 mg/kg of animal body weight.

The compounds of this invention may be administered, dissolved or suspended in any conventional nontoxic pharmaceutical carrier of the type that may be taken orally, applied intranasally, bucally or parenterally. Any suitable carrier may be employed, such as, for example, 15% aqueous hydroxyethylcellulose or the like.

The antiviral activity of the compounds of this invention was measured by well recognized tests. In one type of in vivo test, mice were treated with doses of antiviral compositions of this invention in both pre-challenge and post-challenge administrations. The survival of the drug-treated infected mice was observed over a 9 to 10 day experimental period.

According to this invention the novel bis-basic ethers of 2,6-and 2,7-dihydroxyanthraquinones may be prepared by various methods, such as, for example, according to the methods described in the specific examples and in the several reaction mechanisms illustrated hereinafter wherein A, $R^3$ and $R^4$ have the meanings set forth hereinabove and X is a reactive halogen atom, such as, for example, chlorine, bromine or iodine.

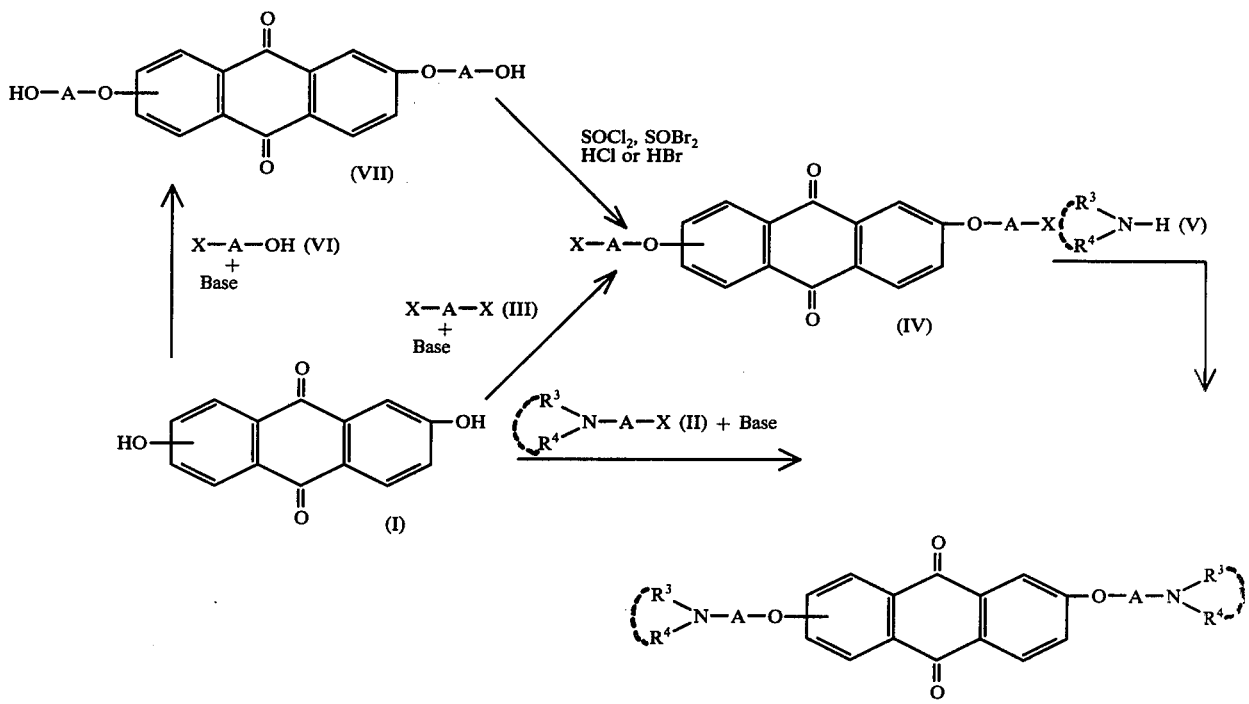

In all the hereinbefore exemplified reaction schemes the starting material (I) is either 2,6-dihydroxyanthraquinone, that is, anthraflavic acid, which is commercially available, or 2,7-dihydroxyanthraquinone, that is isoanthraflavic acid, which can be prepared by the method of J. Hall and A. G. Perkin, *J. Chem. Soc. (London)*, 123, 2036 (1923).

As examples of typical haloalkylamines (II) that may be employed there may be mentioned for example, N,N-diethyl-2-chloroethylamine, N,N-dimethyl-3-chloropropylamine, N-(2-chloroethyl)piperidine and the like.

As examples of typical dihaloalkanes (III) that may be employed there may be mentioned for example, 1-bromo-2-chloroethane, 1,3-dibromopropane and the like. As examples of amines (V) which may be employed are primary amines, such as, for example, methylamine, ethylamine and the like, or secondary amines, such as, for example, dimethylamine, and diisopropylamine and the like.

As examples of typical haloalkanols (VI) which may be employed there may be mentioned for example, 2-chloroethanol, 2-bromoethanol, 3-chloropropanol, 3-bromopropanol and the like.

In the above reaction schemes the base used may be any suitable base, such as, for example, sodium hydroxide, potassium hydroxide, sodium methoxide, sodium hydride, sodium amide, sodium carbonate, potassium carbonate and the like.

The reactions can be carried out either in the presence or absence of suitable solvents. As examples of suitable solvents which may be used as the reaction medium in the above reactions there may be mentioned, for example: aromatic hydrocarbons, such as benzene, toluene, xylene and the like; halogenated aromatic hydrocarbons such as chlorobenzene and the like, aprotic solvents such as N,N-dimethylformamide, N,N-dimethylacetamide, dimethylsulfoxide and the like; alcohols such as ethanol; isopropanol, butanol and the like; ethers such as tetrahydrofuran, dioxane and the like; ketones such as acetone, butanone and the like; water; or suitable mixtures of such solvents.

In preparations where either sodium methoxide, sodium hydride, or sodium amide, for example, is used as the base, the reaction is carried out in an anhydrous medium, such as anhydrous toluene, xylene, chlorobenzene, dimethylformamide, dimethylsulfoxide and the like. For example, about 2.5 molar equivalents of the base is added to a well stirred solution or suspension or one molar equivalent of the dihydroxyanthraquinone (I) in the anhydrous solvent, and the mixture heated to form the diphenoxide of (I). In the case where sodium methoxide is used, the methanol liberated in the formation of the diphenoxide is usually removed by azeotropic distillation.

About 2.5 molar equivalents of the halide compounds (II), (III) or (VI) is then added and the resulting mixture heated at a temperature which may vary from about 60° C. to about 150° C., depending on the nature and boiling point of the solvent. The reaction period may vary from about three to twenty-four hours. The product is then isolated by any suitable procedures such as extraction, filtration or the like. The bis-basic ether products are then generally isolated as bis-acid addition salts. The above procedure was found to be quite useful for preparing certain bis-basic ethers of Formulae 2 and 3.

In preparations where an alkali hydroxide, such as sodium or potassium hydroxide, is used as the base, several different procedures may be used. In one procedure, about 2.5 molar equivalents of a concentrated aqueous or methanolic solution of about 25–50 per cent of the alkali hydroxide is added to a suspension of one molar equivalent dihydroxyanthraquinone (I) in a suitable aromatic solvent, such as xylene or chlorobenzene. With efficient stirring, this mixture is then heated to boiling, the water or methanol being gradually removed by azeotropic distillation. If necessary during the distillation procedure, more of the aromatic solvent may be added to maintain a more or less constant volume. At the conclusion of the distillation, the essentially anhydrous mixture contains the diphenoxide of (I) suspended in the aromatic solvent. About 2.5 molar equivalent of the halide (II), (III) or (VI) is then added and the reaction carried to completion as described above. This procedure was found to be generally useful for preparing bis-basic ethers of Formulae 2 and 3.

In a second procedure, one molar equivalent of the dihydroxyanthraquinone (I) is dissolved in an aqueous solution of 2 molar equivalents of the alkali hydroxide. This solution is filtered to remove any water-insoluble material, then evaporated to dryness in a rotary evaporator. The solid diphenoxide of (I) is then washed with acetone, filtered, ground to a fine powder, and further dried in a vacuum oven at about 100° C. The dry, solid diphenoxide is suspended in a suitable aromatic solvent, such as xylene or chlorobenzene, or an aprotic solvent such as dimethylformamide, and with efficient stirring, the mixture is heated to gentle reflux. About 2.5 molar equivalents of the appropriate halide (II), (III) or (VI) is added and the reaction carried to completion as previously described. This procedure was useful in preparing bis-basic ethers of 2,6-dihydroxyanthraquinone.

In a third procedure, the reaction is carried out in a hetergeneous medium of water and an aromatic hydrocarbon such as toluene, xylene or the like. For example, one molar equivalent of the dihydroxyanthraquinone (I) is suspended in the aromatic hydrocarbon. A solution of about 2.5 molar equivalents of a hydrohalide salt of the amino halide (II) in the minimum volume of water is then added. With efficient stirring, a 25–50% aqueous solution of the alkali hydroxide, about five molar equivalents, is added and the mixture heated to reflux for a period of about 6 to 24 hours. The product is then isolated from the hydrocarbon layer. If this procedure is used with halides (III) or (VI), two molar equivalents of an aqueous solution of the alkali hydroxide is added to a well stirred suspension of one molar equivalent of dihydroxyanthraquinone (I) in the aromatic hydrocarbon. About 2.5 molar equivalents of the halide (III) or (VI) is then added and the mixture heated to reflux, and the reaction carried to completion.

Water may be used as the reaction medium when employing the reaction routes employing halides (III) or (VI). For example, the one molar equivalent of the dihydroxyanthraquinone (I) is dissolved in an aqueous solution of two molar equivalents of alkali hydroxide. The solution is heated, and with rapid efficient stirring, a large excess of the halide (III) or (VI) is added. The mixture is then heated, as in the previous procedures.

The reaction between the bis(ω-haloalkoxy)anthraquinone (IV) and the amine (V) may be carried out under a variety of conditions. For example, the bis-haloalkyl ether (IV) may be heated together with a large excess of the amine (V), the excess amine serving as both the reaction medium and the hydrohalide acceptor. The reaction may be carried out at the boiling point of the amine, or in the case of a low-boiling amine, under pressure at temperatures above the boiling point of the amine. Or, one molar equivalent of the bis-haloalkyl ether (IV) and four or more molar equivalents of the amine (V) may be heated together in one of a number of different types of solvents, such as, for example, aromatic hydrocarbons, benzene, toluene or the like, or alcohols such as methanol, ethanol, isopropanol or the like; aliphatic ketones such as acetone, butanone or the like; or ethers such as tetrahydrofuran, dioxane or the like. In some cases, it may be advantageous to use only two molar equivalents of the amine (V) for each molar equivalent of the bis-haloalkyl ether (IV), an excess of either powdered sodium or potassium carbonate being used as the acceptor for the hydrohalide generated.

If the intermediate bis(ω-haloalkoxy)anthraquinones (IV) are treated with two molar equivalents or hexamethylene-tetramine per equivalent of (IV) and the resulting bis-quaternary halides are hydrolyzed with alcoholic hydrogen chloride under the conditions of the Delepine reaction, the products will be the bis(ω-aminoalkoxy)anthraquinones, that is, compounds described by Formulae 2 and/or 3 wherein $R^3$ and $R^4$ are both hydrogen. Another method for preparing these bis(ω-aminoalkoxy)anthraquinones is to treat the intermediates (IV) with two molar equivalents of potassium phthalimide per equivalent of (IV), then cleave the resulting bis(phthalimido alkoxy)anthraquinones with mineral acid, alkali hydroxide, or hydrazine hydrate in aqueous alcoholic solution.

If the halogen of the bis-haloalkyl ether (IV) is ether chlorine or bromine, the reaction between (IV) and the amine (V) is usually promoted by either sodium or potassium iodide, added in either a catalytic or stoichiometric amount to the reaction mixture.

Another method for preparing bis-basic ethers of 2,6- and 2,7-dihydroxyanthraquinones of the type represented by the above generic Formulae 2 and 3 is illustrated in the following reaction plan.

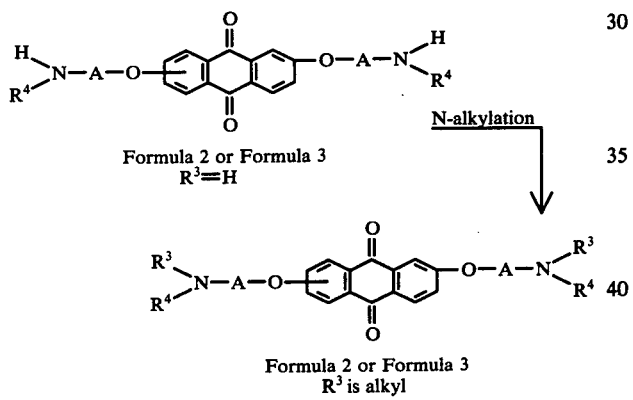

Formula 2 or Formula 3
$R^3 = H$

N-alkylation

Formula 2 or Formula 3
$R^3$ is alkyl

If the starting material is a bis(ω-aminoalkoxy)anthraquinone, that is, both $R^3$ and $R^4$ are H, which can be prepared by the methods given hereinbefore, this bis-primary amine may be alkylated with a large excess of the appropriate alkyl halides to yield the symmetrically substituted bis-tertiary amines, that is, the products wherein $R^3 = R^4 =$ alkyl. Alkylation of such a bis(ω-aminoalkoxy)anthraquinone with formaldehyde and formic acid by the Eschweiler-Clarke procedures yields the bis-tertiary amine wherein $R^3 = R^4 =$ methyl.

If the starting material is a bis(ω-alkylaminoalkoxy)anthraquinone, that is, $R^3 = H$; $R^4 =$ alkyl, which can be prepared by the method illustrated hereinbefore, this bis-secondary amine can also be alkylated with an appropriate alkyl halide to give a bis-tertiary amine wherein both $R^3$ an $R^4$ are alkyl groups, which may be the same or different. Alkylation of such a bis(ω-alkylaminoalkoxy)anthraquinone with formaldehyde and formic acid yields a bis-tertiary amine wherein $R^3$ = methyl and $R^4$ = alkyl which may or may not be methyl. As will be seen, these methods are a convenient method for preparing the bis-tertiary amines wherein $R^3$ and $R^4$ are two different alkyl groups.

The following examples are illustrative of the invention:

EXAMPLE 1

2,6-BIS[2-(DIETHYLAMINO)ETHOXY]ANTHRAQUINONE DIHYDROCHLORIDE

A solution of 12 g. (0.3 mole) of sodium hydroxide in 15 ml. of water was added, with efficient stirring, to a boiling mixture of 36 g. (0.15 mole) of 2,6-dihydroxyanthraquinone suspended in 250 ml. of xylene. With continued stirring, the mixture was heated to reflux, the water being removed from the mixture by collection in a Dean-Stark distilling receiver. When all of the water had been removed, a solution of 2-diethylaminoethyl chloride in 250 ml. of xylene was added. This solution was prepared by dissolving 100 g. (0.58 mole) of 2-diethylaminoethyl chloride hydrochloride in 20 ml. of water, covering the solution with 200 ml. of xylene, chilling the mixture to about −5° C., and with rapid stirring, adding a solution of 45 g. of potassium hydroxide in 35 ml. of water. The xylene layer was decanted from the thick slurry of inorganic salt and water, which was washed with another 50 ml. of xylene. The combined xylene extracts were dried with anhydrous magnesium sulfate and filtered. With continued rapid stirring, the resulting mixture was heated to reflux for another 28 hours. The mixture was poured into 500 ml. of water. The yellow solid which separated at the xylene/water interface was removed by filtration with suction, washed thoroughly with hot water and dried. This major portion of the free base, M.P. 177–180° C., was recrystallized from a mixture of hot methanol and a small volume of chloroform to give the pure base, M.P. 179–180° C. Another 5–10 per cent of base can be obtained by working up the xylene layer. The pure base was dissolved in chloroform, the solution acidified to Congo Red with ethereal hydrogen chloride, diluted with ether, and the yellow precipitate filtered with suction. The dihydrochloride salt obtained was suspended in boiling methanol (15–20 ml. per gram) and a very small volume of water was added to effect solution. This solution was filtered, reduced about one-fourth in volume, diluted with additional methanol, then chilled. The recrystallized dihydrochloride was filtered and dried in a vacuum oven at 100° C. It melted with decomposition at 274–275° C. (or lower if the rate of heating the capillary tube was slower); λmax ($H_2O$) 272, $E_{1cm}^{1\%}$ 863.

EXAMPLE 2

2,6-BIS[2-(DIETHYLAMINO)ETHOXY]ANTHRAQUINONE DIHYDROCHLORIDE

In addition to the method given in Example 1, this compound was also prepared by the following procedure. With efficient stirring, 100 g. (0.42 mole) of 2,6-dihydroxyanthraquinone was dissolved in 500–700 ml. of about 10% potassium hydroxide solution. This solution was filtered to remove a small amount of insoluble material, then evaporated to dryness in a rotary evaporator. The reddish brown solid was dried in a vacuum oven at 100° C., ground to a fine powder, then redried at 100° C. The dry di-potassium diphenoxide weighed 10–25 per cent more than the theoretical yield (132 g. in this case), the excess weight being due to the amount of excess potassium hydroxide used. This amount of the diphenoxide was sufficient for several preparations as described below.

A stirred suspension of 30 g. of the powdered diphenoxide, containing about 24 g. (0.075 mole) of the dipotassium salt of 2,6-dihydroxyanthraquinone, in 200 ml. of xylene was heated to reflux and a small amount of water collected in the Dean-Stark distilling receiver. A solution of 2-diethylaminoethyl chloride in 100 ml. of xylene, prepared as in Example 1 from 50 g. (0.29 mole) of 2-diethylaminoethyl chloride hydrochloride, was then added and the resulting mixture heated to reflux for about 24 hours. The reaction mixture was poured into water and worked up exactly as in Example 1.

In a similar manner, the following four bis-basic ethers of 2,6-dihydroxyanthraquinone and two bis-basic ethers of 2,7-dihydroxyanthraquinone were prepared:

178-181° C. The base can be converted to the dihydrochloride salt as described in Example 1.

Toluene was substituted for chlorobenzene as the organic solvent in the above procedure, but the yield of the pure base obtained was lower, that is, about 30 per cent of the theoretical as compared to about 60 per cent.

EXAMPLE 4

2,6-BIS[2-(DIMETHYLAMINO)ETHOXY]ANTHRAQUINONE DIHYDROCHLORIDE

A well-stirred mixture of 12 g. (0.05 mole) of 2,6-dihydroxyanthraquinone, 400 ml. of chlorobenzene, 50 ml of methanol, and 5.4 g. (0.10 mole) of sodium methoxide was heated to boiling, and the methanol distilled

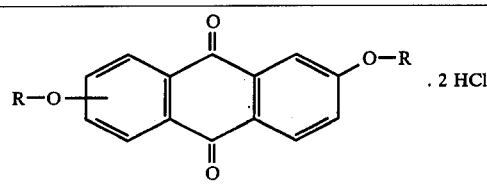

| Positions of R—O— | R | M.P. of base(° C) | M.P. of di-HCl (° C) | max (mµ) | $E^{1\%}_{1\ cm.}$ |
|---|---|---|---|---|---|
| 2.6 | $(i\text{-}C_3H_7)_2NCH_2CH_2$—(1) | 193–194 | 254–256 (dec.) | 274(4) | 776(4) |
| 2.6 | $(CH_3)_2NCH_2CH_2CH_2$—(1) | 119–120 | 288 (dec.) | 275(4) | 835(4) |
| 2.6 | ⟨N⟩CH$_2$CH$_2$—(2) | 139–143 | 286–288 (dec.) | 274(4) | 844(4) |
| 2.6 | ⟨N⟩CH$_2$CH$_2$—(1) | 183–185 | 285–287 (dec.) | 273(4) | 804(4) |
| 2.7 | $(C_2H_5)_2NCH_2CH_2$—(3) | not isolated | 232–234 (dec.) | 275(5) | 1070(5) |
| 2.7 | ⟨N⟩CH$_2$CH$_2$—(3) | not isolated | 275–277 (dec.) | 274(5) | 1057(5) |

(1)Reaction period was seventy-two hours.
(2)Reaction period was forty-eight hours.
(3)Reaction period was twenty-four hours.
(4)In water.
(5)In 95% ethanol.
dec. = decomposition

EXAMPLE 3

2,6-BIS[2-(DIETHYLAMINO)ETHOXY]ANTHRAQUINONE DIHYDROCHLORIDE

In addition to the methods given in Examples 1 and 2, the following method has also proven useful. To a mixture of 114g (0.6 mole) of 2,6-dihydroxyanthraquinone and 1.2 liters of chlorobenzene was added a solution of 412g (2.4 moles) 2-diethylaminoethyl chloride hydrochloride in 350 ml. of water. With efficient stirring, a solution of 264g (4.0 moles) of potassium hydroxide pellets (85%) in 350 ml. of water was added. The resulting mixture was heated with continued stirring on a steam bath for about 24 hours, then cooled by adding about 500 g of ice. 400 ml. chloroform was added. The lower organic layer was separated and washed several times with water, then dried with anhydrous magnesium sulfate. After filtration, the solvents were removed under reduced pressure in a rotary evaporator. The residue was recrystallized from a mixture of methanol and chloroform as described in Example 1 to give 2,6-bis 2-(diethylamino)ethoxy anthraquinone base, M.P.

from the mixture. When the boiling point of the distillate had reached about 130° C., the mixture was allowed to cool below 100°. Then, a solution of 2-dimethylaminoethyl chloride is 200 ml. of chlorobenzene, prepared from 43.2 g. (0.30 mole) of 2-dimethylaminoethyl chloride hydrochloride, was added and the resulting mixture heated to reflux with continued stirring for 24 hours. When cool, the mixture was poured into 400 ml. of about one per cent sodium hydroxide solution. The aqueous layer was extracted with chloroform. The combined organic fractions were washed well with water, dried over anhydrous magnesium sulfate, filtered, and the solvents removed under reduced pressure in a rotary evaporator. The residue was dissolved in isopropanol and the solution acidified to Congo Red by the addition of ethereal hydrogen chloride. The dihydrochloride salt was recrystallized again from isopropanol to give the pure compound, M.P. 278–280° C. (dec.) λmax. (H$_2$O) 273 µ, $E^{1\%}_{1cm.}$ 967.

EXAMPLE 5

2,7-BIS[2-(DIMETHYLAMINO)ETHOXY]ANTHRAQUINONE DIHYDROCHLORIDE

This compound was prepared by the method of Example 4 from 2,7-dihydroxyanthraquinone with the exception that toluene was substituted for chlorobenzene as the reaction medium. The dihydrochloride salt was recrystallized twice from butanone with enough methanol added to effect solution. The product isolated was a hemihydrate, M.P. 230–233° C. (dec.); λmax (95% ethanol) 273, $E_{1cm.}^{1\%}$ 1150.

EXAMPLE 6

2,6-BIS(2-MORPHOLINOETHOXY)ANTHRAQUINONE DIHYDROCHLORIDE

This compound was prepared by the method of Example 3, with the exception that toluene was used as the reaction medium rather than chlorobenzene, from 36 g. (0.15 mole) of 2,6-dihydroxyanthraquinone, 100 g. (0.54 mole) of N-(2-chloroethyl) morpholine hydrochloride, 66g. (1.0 mole) of potassium hydroxide pellets (85%), 400 ml. of toluene and 100 ml. of water. The dihydrocholoride salt was recrystallized twice from isopropanol with enough water added to effect solution. The pure compound melted with decomposition at 288–290° C.; λmax (H₂0) 273 μ, $E_{1cm.}^{1\%}$ 778.

EXAMPLE 7

2,6-BIS[3-(DIETHYLAMINO)PROPOXY]ANTHRAQUINONE DIHYDROCHLORIDE

A mixture of 12 g. (0.05 mole) of 2,6-dihydroxyanthraquinone, 16.5 g (0.11 mole) of 3-diethylaminopropyl chloride, 48 ml. of 10% sodium hydroxide solution, and 100 ml. of dimethylsulfoxide was stirred and heated on a steam bath for two hours. When cool, the mixture was poured into about 500 ml. of water. The solid which precipitated was filtered with suction and washed with water. The crude wet solid was dissolved in chloroform. This solution was dried over anhydrous magnesium sulfate, filtered, and the filtrate acidified to Congo Red with ethereal hydrogen chloride. After dilution with anhydrous ether, the yellow solid was filtered and dried. After two recrystallizations from 95% ethanol, the dihydrochloride (a hydrate) melted with decomposition at 273.5–274.5° C; λmax (H₂O) 274, $E_{1cm.}^{1\%}$ 761.

EXAMPLE 8

By the method of Example 4, but substituting 2,7-dihydroxyanthraquinone for 2,6-dihydroxyanthraquinone, and substituting for 2-dimethylaminoethyl chloride, the appropriate priate molar equivalent quantity of either 3-dimethylaminopropyl chloride, 3-diethylaminopropyl chloride, 2-diisopropylaminoethyl chloride, N-(2-chloroethyl)pyrrolidine, or N-(2-chloroethyl)morpholine, the following five compounds are also prepared:

2,7-Bis[3-(dimethylamino)propoxy]anthraquinone dihydrochloride, 2,7-Bis[3-(diethylamino)propoxy]anthraquinone dihydrochloride, 2,7-Bis[2-(diisopropylamino)ethoxy]anthraquinone dihydrochloride, 2,7-Bis(2-pyrrolidinoethoxy)anthraquinone dihydrochloride and 2,7-Bis(2-morpholinoethoxy)anthraquinone dihydrochloride.

EXAMPLE 9

2,6-BIS(2-chloroethoxy)anthraquinone (A) With efficient stirring, a mixture of 24 g (0.10 mole) of 2,6-dihydroxyanthraquinone and 86 g (0.60 mole) 1-bromo-2-chloroethane in 400 ml of water is heated to reflux, and over a period of thirty minutes, 115 ml. (0.20 mole) of 10% potassium hydroxide is added dropwise. The resulting mixture is then heated to gentle reflux for 12-15 hours. When the mixture is cool, another 100 ml. of 10% potassium hydroxide is added and the product extracted into chloroform. The chloroform extract is washed with 10% potassium hydroxide, then water, and dried over anhydrous magnesium sulfate. After filtration, the filtrate is evaporated to dryness in a rotary evaporator. The residual 2,6-bis(2-chloroethoxy)anthraquinone may be used without further purification, or it can be recrystallized from ethanol, or a mixture of ethanol and a small volume of chloroform.

(B) This compound is also prepared in two steps as follows:

2,6-Bis(2-hydroxyethoxy)anthraquinone can be prepared as in (A) above by substituting 75 g. (0.60 mole) of 2-bromoethanol for 1-bromo-2-chloroethane. Then, with stirring, 25 g. of thionyl chloride is added to a mixture of 20 g. (0.06 mole) of the 2,6-bis(2-hydroxyethoxy)anthraquinone and 0.5 ml. of pyridine in 200 ml. of chloroform. The mixture is heated to reflux on a steam bath for six hours, after which the excess thionyl chloride and chloroform are removed under reduced pressure. The residue is dissolved in chloroform and the solution washed with saturated sodium bicarbonate solution and water, then dried with anhydrous magnesium sulfate. As in (A) above, the 2,6-bis(2-chloroethoxy) anthraquinone is isolated and recrystallized, if needed.

By either of the methods above (A) or (B), 2,7-bis (2-chloroethoxy)anthraquinone is also prepared by substituting 2,7-dihydroxyanthraquinone for 2,6-dihydroxyanthraquinone.

EXAMPLE 10

2,6-BIS(2-AMINOETHOXY)ANTHRAQUINONE (A) 2,6-Bis(2-phthalimidoethoxy)anthraquinone is the first intermediate.

A stirred mixture of 18 g. (0.05 mole) of 2,6-bis(2-chloroethoxy)anthraquinone, prepared as described in Example 9, 5.0 g. of potassium iodide, and 225 ml. of N,N-dimethylformamide is heated on a steam bath for 30 minutes. Then, 20.5 g. (0.11 mole) of potassium phthalimide is added, and with continued stirring, the mixture is heated on the steam bath (about 90° C.) for another 3 hours. When cool, 300 ml. of chloroform is added, and the resulting mixture poured with stirring into 1 liter of water. The chloroform layer is washed with 0.1 N sodium hydroxide, then with water, and dried over anhydrous magnesium sulfate. After filtration, the chloroform is evaporated. The crystalline residue may be used without further purification, or recrystallized from methanol or methanol to which a small amount of water is added.

(B) A mixture of 17.4 g (0.03 mole) of the intermediate 2,6-bis-(2-phthalimidoethoxy)anthraquinone, prepared in (A) above, 200 ml. of methanol, and 3.6 g. (0.06 mole) of hydrazine hydrate (85%) is heated to reflux for four hours. Water (100 ml.) is added and the methanol boiled out of the mixture. Then, 75 ml. of 37% hydrochloric acid is added and the resulting mixture heated to reflux for another hour. The mixture is allowed to cool, then chilled at 0° C., and the precipitate of phthalhydrazide removed by filtration with suction. The filtrate is evaporated to dryness, made alkaline with 10% sodium hydroxide, and the base is extracted into chloroform. The chloroform layer is washed with water, dried with anhydrous magnesium sulfate, filtered, and the chloroform evaporated. The 2,6-bis-(2-aminoethoxy)anthraquinone base is converted to the dihydrochloride salt as described in Example 1, and recrystallized from a solvent or solvent mixture such as isopropanol, ethanol/ether, or butanone/methanol. In a similar manner, 2,7-bis(2-aminoethoxy)anthraquinone can be prepared from 2,7-bis(2-chloroethoxy)anthraquinone.

EXAMPLE 11

2,6-BIS[2-(DIMETHYLAMINO)ETHOXY]ANTHRAQUINONE DIHYDROCHLORIDE

In addition to the method described in Example 4, this compound is also prepared by the following procedure. A mixture of 8.2 g. (0.025 mole) of 2,6-bis(2-aminoethoxy)anthraquinone, prepared as in Example 10, 25 g. of 90% formic acid, and 25 ml. of 37% formaldehyde solution is heated carefully until the vigorous evolution of gases ceases, after which the mixture is heated to reflux for about three hours. After evaporation of the mixture to dryness, the residue is treated with excess 10% sodium hydroxide solution, and the product extracted into chloroform. The chloroform extract is washed well with water, dried with anhydrous magnesium sulfate, filtered, acidified with ethereal hydrogen chloride and the mixture diluted with anhydrous ether. The dihydrochloride salt is purified by recrystallization from isopropanol or isopropanol/methanol as in Example 4.

In a similar manner, 2,7-bis[2-(dimethylamino)ethoxy]anthraquinone dihydrochloride is prepared from 2,7-bis(2-aminoethoxy)anthraquinone.

EXAMPLE 12

2,6-BIS[2-(ETHYLAMINO)ETHOXY]ANTHRAQUINONE

A mixture of 9.0 g. (0.025 mole) of 2,6-bis(2-chloroethoxy)anthraquinone (Example 9), 4.0 g. of potassium iodide, 30 ml. of 70% aqueous ethylamine, and 100 ml. of tetrahydrofuran is heated with stirring at 125° C. for 20 hours in an autoclave. The reaction mixture is evaporated to dryness in a rotary evaporator, diluted with water, made acidic to Congo Red with hydrochloric acid, and the resulting mixture filtered or extracted with chloroform to remove unreacted starting material. The aqueous layer is made alkaline with 10% sodium hydroxide, and the product extracted into chloroform. The chloroform extract is washed with water, dried with anhydrous magnesium sulfate, filtered, and the chloroform evaporated. The 2,6-bis[2-(ethylamino) ethoxy]anthraquinone base can be converted to the dihydrochloride salt as previously described, for example, in Example 1. In a similar manner, 2,7-bis[2-(ethylamino) ethoxy]anthraquinone is prepared from 2,7-bis(2-chloroethoxy)anthraquinone.

EXAMPLE 13

2,6-BIS[2-(DIETHYLAMINO) ETHOXY]ANTHRAQUINONE DIHYDROCHLORIDE

In addition to the methods described in Examples 1, 2 and 3, this compound is also prepared by the following method. A mixture of 9.5 g. (0.025 mole) of 2,6-bis[2-(ethylamino) ethoxy]anthraquinone (Example 12), 5.5 g. (0.05 mole) of ethyl bromide, 10 g. of powdered anhydrous sodium carbonate, and 250 ml. of ethanol is heated with stirring at 145–150° C. for 16 hours in an autoclave. The reaction mixture is poured into about 500 ml. of water, and the solid filtered with suction. The wet solid is dissolved in chloroform, and the solution washed with water, dried with anhydrous magnesium sulfate, filtered, etc. The product is isolated and purified as described in Example 1. In a similar manner, 2,7-bis[2-(diethylamino) ethoxy]anthraquinone is prepared from 2,7-bis [2-(ethylamino) ethoxy]anthraquinone.

In the compounds of this invention the basic ether groups are in positions which are separated from the carbonyl functions of the anthraquinone nucleus by at least two ring carbon atoms and said basic ether groups are in separate benzenoid rings. It has been found that such compounds have unobviously superior antiviral activity and potency, particularly with oral administration, when compared to similar type bis-basic ether of dihydroxyanthraquinones having the basic ether groups in positions which are separated from the carbonyl functions of the anthraquinone nucleus by only one ring carbon atom. Compounds of this latter type are described, for example, in U.S. Pat. No. 2,881,173 of Wilhelm Wenner, as having anthelmintic and antiprotozoan activity. When prepared and tested under comparable test conditions, bis-basic ethers of dihydroxyanthraquinones of the Wenner patent disclosure were not found to possess effective antiviral activity and potency whereas the bis-basic ethers of dihydroxyanthraquinones of this invention were found to possess remarkably effective and superior antiviral activity and potency.

The compounds of this invention were tested and have been found to have unobviously superior antiviral activity and potency against infections of arbovirus, for example, Semliki Forest and Vesicular Stomatitis, myxovirus, for example, influenza A Equine/New Mex.; poxvirus, for example, Vaccinia IHD; picornavirus, for example, Mengo; and herpes virus, for example, Herpes Simplex.

What is claimed is:

1. A compound selected from a base of the formula

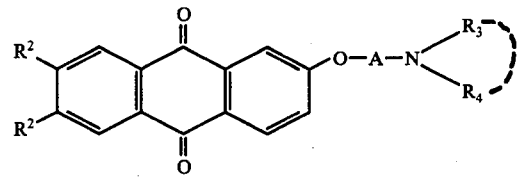

or a pharmaceutically acceptable acid addition salt of said base, wherein one $R^2$ is a hydrogen atom and the other $R^2$ is the radical

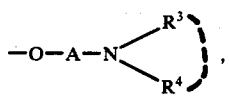

A is a straight chain alkylene group having 2 or 3 carbon atoms and $R^3$ and $R^4$ taken together with the nitrogen atoms to which they are attached is pyrrolidino, piperidino or morpholino.

2. A compound of claim 1 having the formula

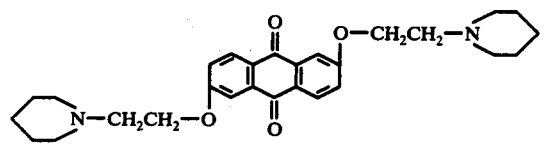

or a pharmaceutically acceptable acid addition salt thereof.

3. A compound of claim 1 having the formula or a pharmaceutically acceptable acid addition salt thereof.

4. A method of resisting as well as suppressing viral infections in a host susceptible to infection which comprises administering to such a host an antivirally effective quantity of a pharmaceutical formulation comprising as the active ingredient a compound of claim 1.

5. The method of claim 4 wherein the administration of the effective quantity of the pharmaceutical formulation is an oral administration of form 0.1 to 500 milligrams of the active ingredient per kilogram of body weight of the host.

6. A pharmaceutical preparation for administration to a host for resisting as well as suppressing viral infections comprising a pharmaceutical carrier and as the active ingredient an antivirally effective quantity of a compound of claim 1.

* * * * *